(12) United States Patent
Chmielewski

(10) Patent No.: US 6,545,195 B2
(45) Date of Patent: Apr. 8, 2003

(54) LOW-DENSITY, SUBSTANTIALLY NON-WICKING LAYERS FOR ABSORBENT ARTICLES

(75) Inventor: Harry J. Chmielewski, Brunswick, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 1 day.

(21) Appl. No.: 09/829,920

(22) Filed: Apr. 11, 2001

(65) Prior Publication Data

US 2003/0045848 A1 Mar. 6, 2003

(51) Int. Cl.$^7$ .................................. A61F 13/15
(52) U.S. Cl. ............... 604/369; 604/385.3; 604/385.23; 604/385.25; 604/367; 604/374; 604/375; 604/378; 604/385.01
(58) Field of Search ................. 604/364, 358, 604/369, 367, 374, 375, 378, 385.01

(56) References Cited

U.S. PATENT DOCUMENTS

| | | | |
|---|---|---|---|
| 4,050,462 A | | 9/1977 | Woon et al. |
| 4,300,562 A | | 11/1981 | Pieniak |
| 4,552,138 A | * | 11/1985 | Hofeditz et al. ............ 424/445 |
| 4,788,225 A | | 11/1988 | Edwards et al. |
| 5,092,861 A | | 3/1992 | Nomura et al. |
| 5,098,423 A | | 3/1992 | Pieniak et al. |
| 5,147,345 A | | 9/1992 | Young et al. |
| 5,268,224 A | | 12/1993 | DesMarais et al. |
| 5,268,244 A | | 12/1993 | Yoo |
| 5,318,554 A | | 6/1994 | Young et al. |
| 5,331,015 A | | 7/1994 | DesMarais et al. |
| 5,336,695 A | * | 8/1994 | Nass et al. ............... 428/304.4 |
| 5,352,711 A | | 10/1994 | DesMarais |
| 5,503,919 A | * | 4/1996 | Litchholt et al. ............ 428/101 |
| 5,550,167 A | * | 8/1996 | DesMarais .................. 521/50 |
| 5,571,849 A | * | 11/1996 | DesMarais ................. 521/146 |
| 5,573,994 A | * | 11/1996 | Kabra et al. ......... 264/DIG. 16 |
| 5,632,737 A | | 5/1997 | Stone et al. |
| 5,692,939 A | | 12/1997 | DesMarais |
| 5,786,396 A | | 7/1998 | Takita et al. |
| 5,810,800 A | * | 9/1998 | Hunter et al. ............... 604/358 |
| 5,851,648 A | | 12/1998 | Stone et al. |
| 5,869,171 A | * | 2/1999 | Shiveley et al. ......... 428/304.4 |
| 6,068,620 A | | 5/2000 | Chmielewski |
| 6,107,538 A | * | 8/2000 | Young et al. ............... 604/358 |
| 6,160,028 A | * | 12/2000 | Dyer .......................... 521/63 |
| 6,372,953 B1 | * | 4/2002 | Young et al. ............... 604/369 |

FOREIGN PATENT DOCUMENTS

| | | | | |
|---|---|---|---|---|
| WO | WO 8801878 | * | 3/1988 | ........... A61L/15/06 |

* cited by examiner

Primary Examiner—John J. Calvert
Assistant Examiner—Angela J Grayson
(74) Attorney, Agent, or Firm—Scott F. Yarnell; Christopher C. Campbell; Hunton & Williams

(57) ABSTRACT

Absorbent articles, such as diapers, incontinence products, training pants, sanitary napkins, and the like, providing unexpectedly superior absorbency and methods of preparing the absorbent articles are disclosed. The absorbent articles comprise a substantially non-wicking layer disposed between a substantially impermeable backsheet and a permeable topsheet, said substantially non-wicking layer comprising foam having a density of no greater than about 0.01 g/cc and a compressional rigidity at about 10% strain of at least about 4 kPa.

55 Claims, No Drawings

LOW-DENSITY, SUBSTANTIALLY NON-WICKING LAYERS FOR ABSORBENT ARTICLES

FIELD OF THE INVENTION

The present invention relates generally to an absorbent composition for absorbent articles such as diapers, incontinence products, training pants, sanitary napkins, and the like. In particular, the present invention is directed to absorbent articles, having unexpectedly superior absorbent properties, comprising a substantially non-wicking layer disposed between a substantially impermeable backsheet and a permeable topsheet, said substantially non-wicking layer comprising foam having a density of no greater than about 0.01 g/cc and a compressional rigidity at about 10% strain of at least about 4 kPa.

BACKGROUND OF THE INVENTION

Disposable absorbent articles typically include a moisture-impervious backing sheet, an absorbent pad, and a liner sheet that contacts the body of a person wearing the article. In addition, elasticized regions are provided around the edges of the article to secure the article about the waist and legs of a wearer. Diapers typically further comprise opposed front and rear waist portions defining a waist opening, a crotch portion disposed there between, and a pair of elastically contractible leg openings along the side edges of the crotch portion. Disposable diapers having elasticized margins for placement about the legs of a wearer are disclosed in U.S. Pat. No. 4,050,462 and U.S. Pat. No. 5,092,861. An absorbent article having elasticized side margins and waist band margins are shown in U.S. Pat. No. 4,300,562.

Despite previous advancements in the field of absorbent articles, persons of ordinary skill in the art continue their efforts to produce absorbent articles having better absorbency and that are thus are better able to contain urinary and fecal excretions. For instance, problems with prior diaper designs include inferior absorbency and leakage of urinary or fecal material from the article. Prolonged contact of liquid or semi-solid excreta with the skin of the wearer is also a continuing problem in the art. For example, the moisture vapor and heat generated by the bodily exuded trapped within a diaper may lead conditions adjacent to wearer's skin which promotes skin irritation, infection, and the like. Various approaches to improve the absorbency of absorbent articles have been attempted, including the incorporation of foams as acquisition layers in the absorbent articles.

For example, U.S. Pat. No. 5,147,345 to Young et al. discloses absorbent articles, such as diapers, for the management of incontinence. Such articles utilize in their absorbent cores a fluid acquisition/distribution component and a fluid storage/redistribution component maintained in fluid communication with the acquisition/distribution component. The fluid acquisition/distribution component can be any porous hydrophilic, e.g., fibrous or foam-based, material which will provide an initial Fluid Acquisition Rate of at least 2 mL of synthetic urine per second and will also preferably provide a 30-minute Vertical Wicking Height of at least 2 cm. The fluid storage/redistribution component comprises a hydrophilic, flexible, open-celled polymeric foam having a free absorbent capacity of at least about 12 mL of synthetic urine per gram of dry foam and an absorbent capacity under a 5.1 kPa confining pressure which is at least 5% of this free capacity. Preferred fluid acquisition/ distribution component materials comprise chemically stiffened, twisted, curled cellulosic fibers. Preferred fluid storage/redistribution component materials comprise absorbent foams prepared by polymerizing a high internal phase emulsion (HIPE).

U.S. Pat. No. 5,318,554 to Young et al. discloses absorbent articles, such as diapers, for the management of incontinence. Such articles utilize in their absorbent cores an fluid acquisition/distribution component and a fluid storage/redistribution component maintained in fluid communication with the acquisition/distribution component. The fluid acquisition/distribution component can be any porous hydrophilic, e.g., fibrous or foam-based, material which will provide an initial Fluid Acquisition Rate of at least 2 mL of synthetic urine per second and will also preferably provide a 30-minute Vertical Wicking Height of at least 2 cm. The fluid storage/redistribution component comprises a hydrophilic, flexible, open-celled polymeric foam having a free absorbent capacity of at least about 12 mL of synthetic urine per gram of dry foam and an absorbent capacity under a 5.1 kPa confining pressure which is at least 5% of this free capacity. Preferred fluid acquisition/distribution component materials comprise chemically stiffened, twisted, curled cellulosic fibers. Preferred fluid storage/redistribution component materials comprise absorbent foams prepared by polymerizing a high internal phase emulsion (HIPE).

U.S. Pat. No. 5,268,224 to Des Marais et al. discloses absorbent foam materials suitable for use as or in the absorbent cores of absorbent articles, such as diapers which absorb and retain aqueous body fluids. Such foam materials comprise hydrophilic, flexible open-celled structures which are preferably prepared by polymerizing high internal phase (HIPE) water-in-oil emulsions. Such foam materials have a pore volume of from about 12 to 100 mL/g, and a capillary suction specific surface area of from about 0.5 to 5.0 m.sup.2/g. These materials also exhibit a resistance to compression deflection such that a confining pressure of 5.1 kPa produces after 15 minutes a strain of from about 5% to 95% compression when the material is saturated at 37 degrees Celsius to its free absorbent capacity with synthetic urine.

U.S. Pat. No. 5,331,015 to DesMarais et al. discloses absorbent foam materials suitable for use as or in the absorbent cores of absorbent articles, such as diapers which absorb and retain aqueous body fluids. Such foam materials comprise hydrophilic, flexible open-celled structures which are preferably prepared by polymerizing high internal phase (HIPE) water-in-oil emulsions. Such foam materials have a pore volume of from about 12 to 100 mL/g, and a capillary suction specific surface area of from about 0.5 to 5.0 m.sup.2/g. These materials also exhibit a resistance to compression deflection such that a confining pressure of 5.1 kPa produces after 15 minutes a strain of from about 5% to 95% compression when the material is saturated at 37 degrees Celsius to its free absorbent capacity with synthetic urine.

U.S. Pat. No. 5,851,648 to Stone et al. discloses absorbent foams materials that are capable of acquiring and distributing aqueous fluids, especially discharged body fluids such as urine. These absorbent foams combine relatively high capillary absorption pressures and capacity-per-weight properties that allow them to acquire fluid, with or without the aid of gravity. These absorbent foams also give up this fluid efficiently to higher absorption pressure storage materials, including foam-based absorbent fluid storage components, without collapsing. These absorbent foams are made by polymerizing high internal phase emulsions (HIPEs).

U.S. Pat. No. 5,786,396 to Stone et al. discloses absorbent foams materials that are capable of acquiring and distributing aqueous fluids, especially discharged body fluids such as urine. These absorbent foams combine relatively high capillary absorption pressures and capacity-per-weight properties that allow them to acquire fluid, with or without the aid of gravity. These absorbent foams also give up this fluid efficiently to higher absorption pressure storage materials, including foam-based absorbent fluid storage components, without collapsing. These absorbent foams are made by polymerizing high internal phase emulsions (HIPEs).

U.S. Pat. No. 5,632,737 to Stone et al. discloses absorbent foams materials that are capable of acquiring and distributing aqueous fluids, especially discharged body fluids such as urine. These absorbent foams combine relatively high capillary absorption pressures and capacity-per-weight properties that allow them to acquire fluid, with or without the aid of gravity. These absorbent foams also give up this fluid efficiently to higher absorption pressure storage materials, including foam-based absorbent fluid storage components, without collapsing. These absorbent foams are made by polymerizing high internal phase emulsions (HIPEs).

U.S. Pat. No. 5,692,939 to DesMarais discloses absorbent foam materials that are capable of acquiring and distributing aqueous fluids, especially discharged body fluids such as urine. These absorbent foams combine relatively high capillary absorption pressures and capacity-per-weight properties that allow them to acquire fluid, with or without the aid of gravity. These absorbent foams also give up this fluid efficiently to higher absorption pressure storage materials, including foam-based absorbent fluid storage components, without collapsing. These absorbent foams are made by polymerizing high internal phase emulsions (HIPEs).

U.S. Pat. No. 5,550,167 to DesMarais discloses absorbent foam materials that are capable of acquiring and distributing aqueous fluids, especially discharged body fluids such as urine. These absorbent foams combine relatively high capillary absorption pressures and capacity-per-weight properties that allow them to acquire fluid, with or without the aid of gravity. These absorbent foams also give up this fluid efficiently to higher absorption pressure storage materials, including foam-based absorbent fluid storage components, without collapsing. These absorbent foams are made by polymerizing high internal phase emulsions (HIPEs).

U.S. Pat. No. 5,352,711 to DesMarais discloses normally hydrophobic foams, such as polyurethane foams and polymerized water-in-oil emulsion foams, are rendered hydrophilic by means of treatment with simple surfactants and hydrophilizing agent salts. Thus, a surfactant-containing foam is treated with a solution of, for example, calcium chloride, and is dried to leave a substantially uniformly distributed residue of hydrated or hydratable calcium chloride on the surfactant-containing internal foam surfaces. In-use, the combination of surfactant and calcium chloride hydrate provides a hydrophilic surface to the foam. Other hydratable calcium or magnesium salts such as magnesium chloride can be used. The resulting hydrophilized foams are suitable for use in absorbent devices, including diapers, sanitary napkins, bandages, and the like.

As is apparent from the foregoing, each of the prior references present a variety of means for improving absorbency in absorbent garments. However, all of these proposed means are deficient in terms of effectiveness and low product quality, mechanical complexity in design, and/or associated cost inefficiencies.

In view of the deficiencies of the various products and processes disclosed in the above discussed references, it is highly desirable to provide cost-efficient absorbent articles that display superior absorbency, as well as novel compositions and composites for use in said absorbent articles. Further, it is highly desirable to provide a cost-efficient process for producing absorbent articles having superior absorbency.

SUMMARY OF THE INVENTION

The present invention provides absorbent articles, and novel compositions and composites for use in same, that display unexpectedly superior absorbency. Further, the present invention provides a cost-efficient process for producing absorbent articles having superior absorbency. Moreover, the present invention provides cost-efficient absorbent articles, methods for preparing and using such articles, and novel compositions and composites for use in same.

One embodiment of the present invention provides an absorbent article comprising: a substantially impermeable backsheet; a permeable topsheet; a substantially non-wicking layer disposed between the substantially impermeable backsheet and the permeable topsheet, said substantially non-wicking layer comprising foam having a density of no greater than about 0.01 g/cc and a compressional rigidity at about 10% strain of at least about 4 kPa.

A further embodiment of the present invention provides an absorbent article comprising: a substantially impermeable backsheet; a permeable topsheet; an absorbent core disposed between the substantially impermeable backsheet and the permeable topsheet; and a substantially non-wicking layer disposed on a surface of the absorbent core, said substantially non-wicking acquisition layer comprising a foam having a density of no greater than about 0.01 g/cc and a compressional rigidity at about 10% strain of at least about 4 kPa.

An even further embodiment of the present invention provides an absorbent garment comprising: a substantially impermeable backsheet and a permeable topsheet defining a front waste portion and a rear waste portion, said front waste portion and said rear waste portion cooperating to form a waste opening; a crotch region formed between the front waste portion and the rear waste portion; a pair of leg openings on opposed sides of the crotch region; an absorbent core; disposed between the substantially impermeable backsheet and the permeable topsheet at the crotch region; and a substantially non-wicking acquisition layer disposed on the absorbent core, said substantially non-wicking acquisition layer comprising a foam having a density of no greater than about 0.01 g/cc and a compressional rigidity at about 10% strain of at least about 4 kPa.

A still further embodiment of the present invention provides a composition for absorbent articles comprising: a foam comprising a polymer selected from the group consisting of, said foam having a density of no greater than about 0.01 g/cc and a compressional rigidity at about 10% strain of at least about 4 kPa.

Yet another embodiment of the present invention provides a composition for absorbent articles prepared by a process comprising: combining a foaming agent and a stabilizing agent to form a High Internal Phase Emulsion (HIPE); polymerizing the High Internal Phase Emulsion (HIPE) to form a substantially non-wicking polymer foam, said substantially non-wicking polymer foam having a density of no greater than about 0.01 g/cc and a compressional rigidity at about 10% strain of at least about 4 kPa.

A further embodiment of the present invention provides a method of preparing an absorbent article comprising: combining a foaming agent and a stabilizing agent to form a High Internal Phase Emulsion (HIPE); polymerizing the High Internal Phase Emulsion (HIPE) to form a substantially non-wicking polymer foam, said substantially non-wicking polymer foam having a density of no greater than about 0.01 g/cc and a compressional rigidity at about 10% strain of at least about 4 kPa.

A still further embodiment of the present invention provides a method of improving absorbency of an absorbent article comprising: applying a substantially non-wicking layer to a surface of an absorbent core, said substantially non-wicking acquisition layer comprising a foam having a density of no greater than about 0.01 g/cc and a compressional rigidity at about 10% strain of at least about 4 kPa a substantially impermeable backsheet; and disposing the absorbent core between a substantially impermeable backsheet and a permeable topsheet.

DETAILED DESCRIPTION OF THE INVENTION

As used herein, the term "absorbent article" refers to articles that absorb and contain exudates, and more specifically refers to articles which are placed against or in proximity to the body of a wearer of the absorbent article to absorb and contain various exudates discharged from the body. A non-exhaustive list of examples of absorbent articles includes diapers, diaper cores, diaper covers, disposable diapers, training pants, feminine hygiene products and adult incontinence products, without limitation. The term "disposable article" refers to absorbent articles that are intended to be discarded or partially discarded after a single use, i.e., they are not intended to be laundered or otherwise restored or reused. The term "unitary disposable absorbent article" refers to a disposable absorbent article that is essentially a single structure (i.e., it does not require separate manipulative parts such as a diaper cover and insert). As used herein, the term "diaper" refers to an absorbent article generally worn by infants and incontinent persons about the lower torso.

The claims are intended to cover all of the forgoing classes of absorbent articles, without limitation, whether disposable, unitary or otherwise. These classifications are used interchangeably throughout the specification, but are not intended to limit the claimed invention. The invention will be understood to encompass, without limitation, all classes of absorbent articles, including those described above. Preferably, the absorbent core is thin in order to improve the comfort and appearance of a garment. The employance of thin, comfortable garments is disclosed, for example without limitation in U.S. Pat. No. No. 5,098,423 to Pineiak et al. which is herein incorporated by reference.

The present invention provides an absorbent article, as well as a method of preparing same and a method of using said absorbent article, having unexpectedly superior properties of absorbency, leakage protection and/or skin wellness. The present invention can be understood by the disclosure herein The present invention is directed to absorbent articles, having unexpectedly superior absorbency properties. In accordance with an implementation of the present invention, absorbent articles comprise a substantially non-wicking layer disposed between a substantially impermeable backsheet and a permeable topsheet, said substantially non-wicking layer comprising foam having a density of no greater than about 0.01 g/cc and a compressional rigidity at about 10% strain of at least about 4 kPa. A further implementation of the present invention provides an absorbent article comprising: a substantially impermeable backsheet; a permeable topsheet; a substantially non-wicking layer disposed between the substantially impermeable backsheet and the permeable topsheet, said substantially non-wicking layer comprising foam having a density of no greater than about 0.01 g/cc and a compressional rigidity at about 10% strain of at least about 4 kPa.

The foam material in accordance with an implementation of the present invention comprises a polymer. Any polymer effective in conferring to the foam the physical characteristics recited herein are suitable. Persons of skill in the art would readily be able to selected and utilize such polymers to implement the present invention, based upon the guidance provided herein. Non-limiting exemplary polymers suitable in implementation of the present invention include polymers selected from the group consisting of polyurethanes, polyethylenes, polypropylenes, polyacrylics, polyamides, polyvinyl chlorides, epoxys, polystyrenes, melamine-formaldehyde polymers and combinations thereof. Preferably, the polymer is a polyurethane, melamine-formaldehyde polymer or combination thereof. More preferably, the polymer is a melamine-formaldehyde polymer.

The foams suitable for the absorbent articles of the present invention have a density no greater than about 0.01 g/cc. Preferably, the foam has a density no greater than about 0.007 g/cc. More preferably, the foam has a density no greater than about 0.005 g/cc. Even more preferably, the foam has a density no greater than about 0.004 g/cc. The preparation of such forms and their incorporation into absorbent articles is described in further detail below and may be accomplished using conventional techniques and methods well known in the art. Persons of ordinary skill in the art would be readily able to prepare and identify foams meeting these characteristics, without undue experimentation, based upon the guidance provided herein.

The foams suitable for the absorbent articles of the present invention have a compressional rigidity at 10% strain of at least about 4.5 kPa. Preferably, the foam has a compressional rigidity at 10% strain of at least about 5.0 kPa. More preferably, the foam has a compressional rigidity at 10% strain of at least about 5.5 kPa. Methods for measuring the compressional rigidity are described below. The preparation of such forms and their incorporation into absorbent articles is described in further detail below and may be accomplished using conventional techniques and methods well known in the art. Persons of ordinary skill in the art would be readily able to prepare and identify foams meeting these characteristics, without undue experimentation, based upon the guidance provided herein.

Optionally, the foam additionally comprises a stabilizing agent. The stabilizing agent may be a crosslinking agent. Non-limiting exemplary stabilizing agents include formaldehyde, glutaraldehyde, glyoxal, glyoxylic acid, oxydisuccinic acid, citric acid, a dialdehyde having 2 to 8 carbon atoms, a monoaldehyde having an acid functionality and 2 to 8 carbon atoms, a polycarboxylic acid having 2 to 9 carbon atoms, and combinations thereof. The stabilizing agent is preferably selected from the group consisting of formaldehyde, glutaraldehyde, glyoxal, glyoxylic acid, oxydisuccinic acid, citric acid and combinations thereof. When the stabilizing agent is a crosslinking agent, the crosslinking agent may be selected from the group consisting of a dialdehyde having 2 to 8 carbon atoms, a monoaldehyde having an acid functionality and 2 to 8 carbon atoms, a polycarboxylic acid having 2 to 9 carbon atoms, and combinations thereof. Most preferably, the foam comprises melamine resin and formaldehyde.

The substantially non-wicking layer may additionally comprise a surfactant, a filler, an additive or a combination thereof. Preferably, the additive is selected from the group consisting of flame retardants, reinforcing agents, auxiliary blowing agents, medicaments, fragrances, colorants, cleaners, abrasives and combinations thereof.

The absorbent article is optionally a diaper, incontinent brief, training pant, diaper holder, diaper liner, sanitary napkin, hygienic garment or combinations thereof. Diapers may include daytime diapers, nighttime diapers, long-term wear diapers, travel diapers, swimming diapers, daytime/nighttime diapers, male diapers, female diapers, unisex diapers, active diapers, seasonal diapers, cold weather diapers, warm weather diapers, medicated diapers or combinations thereof.

The substantially non-wicking layer may be formed in a variety of ways and the inventions is not intended to be limited to any specific manner of formation. Preferably, the substantially non-wicking layer is thermo-formed. Even more preferably, the substantially non-wicking layer is thermo-bonded to the substantially impermeable backsheet or the permeable topsheet.

The physical characteristics of the foams in accordance with an implementation of the present invention are determined by various factors. These factors include density of the foam, and foam flexibility and compression deflection characteristics. These factors also influence the cost effectiveness of the absorbent articles.

Foam density in grams of foam per cubic centimeter of foam volume in air is specified herein on a dry basis. Thus, the amount of absorbed aqueous liquid, e.g., that residual liquid which may be left in the foam, for example, after HIPE emulsion polymerization, washing and/or hydrophilization, is disregarded in calculating and expressing foam density. Foam density as specified herein does include, however, residual solid material such as electrolyte, emulsifiers, hydrophilizing agents, and the like, in the polymerized foam. Such residual material may, in fact, contribute significant mass to the foam material. Persons of ordinary skill in the art would readily be able to use a variety of conventional techniques to produce foams in accordance with an implementation of the present invention.

Any suitable procedure which will provide a determination of mass of solid foam material per unit volume of foam structure can be used to measure foam density. For those situations where the foam sample preparation procedures (drying, aging, preflexing, etc.,) might inadvertently alter the density measurements obtained, then alternate density determination tests may also be utilized. Such alternative methods, for example, might include gravimetric density measurements using a test liquid absorbed within the foam material. This type of density determination method can be useful for characterizing very low density foams such as the foams herein wherein the dry density approximates the inverse of the pore volume of the foam. [See Chatterjee, "Absorbency," Textile Science and Technology, Vol. 7, 1985, p. 41.] As with pore volume and capillary suction specific surface area, the ranges for foam density set forth hereinafter are intended to be inclusive, i.e., they are intended to encompass density values that may be determined by any reasonable experimental test method.

The foam absorbents of the present invention will preferably have dry basis density values of no greater than about 0.01 g/cc, preferably no greater than 0.007 g/cc, more preferably no greater than about 0.005 g/cc, and even more preferably no greater than about 0.004 g/cc, at the time such foam absorbents encounter aqueous fluids to be absorbed. Density of foam materials can be adjusted to within the foregoing ranges by controlling many of the same foam composition and processing parameters set forth hereinbefore for pore volume adjustment. Density of the foam may be uniform throughout the structure or non-uniform. Some portions or zones of the foam structure may have relatively higher or lower densities than other portions or zones thereof.

Foam cell size, although not an essential parameter, may be useful in defining preferred foam materials of this invention, is cell size. Foam cells, and especially cells which are formed by polymerizing a monomer-containing oil phase that surrounds relatively monomer-free water-phase bubbles, will frequently be substantially spherical in shape. The size or "diameter" of such substantially spherical cells is thus yet another commonly utilized parameter for characterizing foams in general as well as for characterizing certain preferred absorbent foams of the type utilized in the present invention. Since cells in a given sample of polymeric foam will not necessarily be of approximately the same size, an average cell size, i.e., average cell diameter, will often be specified.

Cell size, like foam density, capillary suction specific surface area and pore volume, can also impact on the characteristics of the foam, in accordance with an implementation of the present invention. Since cell size is a factor, along with capillary suction specific surface area, pore volume and foam hydrophilicity, that determines the capillarity of the foam, cell size is a foam structure parameter that can directly affect both the absorbent capacity and the internal fluid wicking properties of the foam absorbents herein. Cell size can also affect mechanical properties of the foam absorbents herein including such features as flexibility and resistance to and recovery from compression deflection.

A number of techniques are available for determining average cell size in foams. These techniques include mercury porosimetry methods which are well known in the art. Another technique for determining cell size in foams involves simple photographic measurement of a foam sample. For example, a photomicrograph of a fracture surface of a typical HIPE foam absorbent structure of the present invention is taken. Superimposed on the photomicrograph is a scale representing a dimension of 10 microns. Such a scale can be used to determine average cell size via an image analysis procedure. Image analysis of photomicrographs of foam samples is, in fact, a commonly employed analytical tool which can be used to determine average cell size of the foam structures herein. Such a technique is described in greater detail in U.S. Pat. No. 4,788,225, issued to Edwards et al. on Nov. 29, 1988, which is incorporated herein by reference.

Size or diameter of the cells in the foam absorbents herein can be influenced and controlled by variation of the same type of foam composition and processing features that influence capillary suction specific surface area and available pore volume. For the preferred HIPE-based foams, these include primarily those factors which determine the size of the water-phase "bubbles" in the HIPE emulsion precursor of the polymeric foam structures herein. Thus, cell size can be varied by adjusting water-to-oil ratio of the HIPE emulsion, and the type and amount emulsifier used to form the HIPE emulsion. Cell size may also be altered by simply compressing the solid foam structures after they have been prepared.

As indicated hereinbefore, the dimensions of cells in the absorbent foams of this invention will generally not be uniform so an average cell size for any given foam sample or zone in a foam sample can and should be calculated. It is, of course, possible to utilize absorbent foams which have discrete, identifiable zones of relatively larger or relatively smaller average cell size.

Persons of ordinary skill in the art would be readily able to vary the cell size and other characteristics discussed herein to obtain foams in accordance with the present invention, using conventional materials and techniques. Further, various techniques and methods for measuring such characteristics are well known in the art. For example, various such techniques are described in U.S. Pat. No. 5,268,224, issued to DesMarais et al. on Dec 7, 1993, which is incorporated herein by reference in its entirety.

Absorbent foams having suitable polymeric composition and the structural features hereinbefore described will, in general, possess mechanical properties, e.g., resistance to compression deflection, flexibility, recovery from compression deflection, integrity, softness, etc., which render such foams suitable for use as absorbent structures in absorbent articles such as disposable diapers. Within the aforementioned structural limitations, however, it is possible to select certain combinations of parameters and/or certain foam preparation techniques and conditions which provide foam absorbents that exhibit especially desirable mechanical properties. The specific, somewhat interrelated mechanical properties which have been identified as contributing to the realization of absorbent foams especially suitable for use in absorbent articles for incontinence management can be summarized as follows:

The primary mechanical characteristic of the foams of the present invention is the strength of the foam as determined by compressional rigidity at the recited densities. By way of theory, without intending to be limited thereto, the compressional rigidity exhibited by the foam is a function of the polymer elastic modulus and the matrix structure of the forms. The elastic modulus is, in turn, determined by the polymeric composition of the matrix and/or the extent to which the matrix may be plasticized by residual material, e.g., emulsifiers, synthesis water phase or subsequently added hydrophilizing agents, left in the foam structure after processing.

Vertical wicking performance is related to the magnitude of the capillary suction driving force which moves liquid through the foam and holds it in the foam structure. Foam characterizing parameters which relate to vertical wicking propensity thus provide an indication as to how well preferred foams herein will perform as absorbent structures in absorbent articles. For the foams of the present invention, fluid wicking propensity can be quantified by referencing both a vertical wicking rate test and a vertical wicking absorbent capacity test.

The vertical wicking rate test measures the time taken for a colored test liquid (e.g., synthetic urine) from a reservoir to wick a vertical distance of 5 cm through a test strip of foam of specified size when the test is performed at 37 degrees Celsius.

The vertical wicking absorbent capacity test may carried out in conjunction with the vertical wicking rate test. Vertical wicking absorbent capacity measures the amount of test fluid per gram of absorbent foam that is wicked to each one inch (2.54 cm) vertical section of the same standard size foam sample used in the vertical wicking rate test. Such a determination is generally made after the sample has been allowed to vertically wick test fluid to equilibrium. Like the vertical wicking rate test, the vertical wicking absorbent capacity test is described below. It is preferred that the vertical wicking absorbent capacity and the vertical wicking rate are minimized.

Foams suitable for the absorbent articles of the present invention may be prepared from high internal phase emulsions ("HIPEs" or "HIPE" emulsions). HIPES are formed from polymerization of certain water-in-oil emulsions having therein a relatively high ratio of water phase to oil phase. The relative amounts of the water and oil phases used to form the polymeric foam precursor HIPE emulsions are, among many other parameters, important in determining the structural, mechanical and performance properties of the resulting preferred polymeric foams. In particular, the ratio of water to oil in the foam-forming emulsion can influence foam density, cell size, specific surface area of the foam and dimensions of the struts which form the foam. The preparation of foams from HIPE emulsions is described in U.S. Pat. No. 5,268,224, issued to DesMarais et al. on Dec. 7, 1993, which is incorporated herein in its entirety. Persons of ordinary skill in the art would be readily able to prepare foams in accordance with an implementation of the present invention, based upon the guidance provided herein.

The chemical nature, makeup and morphology of the polymer that forms the foam herein is determined by both the type and concentration of the monomers, comonomers and crosslinkers utilized in the HIPE emulsion and by the emulsion polymerization conditions employed. Such polymeric material will generally be non-swellable in aqueous liquids in that the material itself does not significantly plasticize or imbibe aqueous liquids it contacts. However, no matter what the particular monomeric makeup, molecular weight or morphology of the polymeric material might be, the resulting preferred polymeric material will generally be viscoelastic in character. Thus, the polymer of the preferred foam structures herein will possess both viscous, i.e., fluid-like, properties and elastic, i.e., spring-like, properties. It is important that the polymeric material which forms the cellular foam structure have physical, rheological, and morphological attributes which, under conditions of use, impart suitable flexibility, resistance to compression deflection, and dimensional stability to the absorbent foam material.

The absorbent foam materials of the present invention can be prepared using any suitable polymerization and post-polymerization process steps and using any suitable combination of monomeric materials, so long as hydrophilic foams result which have the hereinbefore described essential, and if desired preferred, structural and mechanical characteristics. As noted, a preferred method of realizing polymeric foams having the requisite structural and mechanical characteristics, and having the desired fluid handling properties, involves the polymerization of High Internal Phase Emulsions (HIPEs). Preparation of foams will thus be described to illustrate how foams of the type envisioned herein can be made.

For example, the foam is prepared by forming a stable high internal phase emulsion (HIPE), thereafter polymerizing this stable emulsion under conditions suitable for forming a solid polymeric foam structure, washing and, if necessary, hydrophilizing the solid polymeric foam structure by treating the structure with water and/or liquid-form hydrophilizing agents to remove the original residual water phase from the polymeric foam structure and to deposit any needed hydrophilizing agent, and thereafter dewatering this polymeric foam structure to the extent necessary to render the foam material useful as an absorbent for aqueous body fluids. Each of these basic process steps is described in greater detail as follows:

The HIPE emulsion precursor to a foam in accordance with absorbent materials herein can be formed by combining an oil phase with a water phase. The oil phase used to form the HIPE emulsions herein will contain the hereinbefore specified essential components such as the requisite monomers, comonomers, cross-linkers and emulsifiers. The oil phase may also contain optional components such as solvents and polymerization initiators. The water phase used to form the HIPE emulsions herein will contain the hereinbefore specified electrolyte as an essential component and may also contain optional components such as water-soluble emulsifiers, and/or polymerization initiators.

The HIPE emulsion can be formed from the combined oil and water phase by subjecting this combination of phases to shear agitation. Shear agitation is generally applied to the extent and for a time period necessary to form a stable emulsion from the combined oil and water phases. Such a process may be conducted in either batchwise or continuous fashion and is generally carried out under conditions suitable for forming an emulsion wherein the oil phase droplets are dispersed to such an extent that the polymerized foam which is eventually formed from the emulsion will have the requisite pore volume and other structural characteristics. Emulsification of the oil and water phase combination will frequently involve the use of a mixing or agitation device such as a pin impeller.

The HIPE emulsion, formed as described hereinbefore, will generally be placed in a suitable reaction vessel, container or region to be polymerized. In one implementation herein, the reaction vessel comprises a tub constructed of polyethylene from which the eventually polymerized solid foam material can be easily removed for further processing after polymerization has been carried out to the extent desired.

Polymerization conditions to which the HIPE emulsion will be subjected will vary depending upon the monomeric and other makeup of the oil and water phases of the emulsion and the type and amounts of polymerization initiators utilized.

The solid HIPE foam which is formed upon completion of the hereinbefore described polymerization step will generally be a flexible, open-cell porous structure having its cells filled with the residual water phase material which was used to prepare the HIPE emulsion prior to polymerization. This residual water phase material, which generally comprises an aqueous solution of electrolyte, residual emulsifier, and polymerization initiator, should be removed from the foam structure at this point prior to further processing and use of the foam. Removal of the original water phase material will usually be carried out by compressing the foam structure to squeeze out residual liquid and/or by washing the foam structure with water and/or other aqueous washing solutions. Frequently several compressing and washing steps, e.g., 2 cycles, will be utilized.

After the original water phase material has been removed from the foam structure to the extent required, the HIPE foam may need to be treated, i.e., by continued washing, with an aqueous solution of a suitable hydrophilizing agent. Hydrophilizing agents which may be employed are listed hereinbefore. As noted, treatment of the HIPE foam structure with the hydrophilizing agent solution continues, if necessary, until the desired amount of hydrophilizing agent has been incorporated and until the foam exhibits a desired adhesion tension value for any test liquid of choice.

After the HIPE foam has been treated to the extent necessary to render the eventually dried foam suitably hydrophilic, the foam will generally be dewatered prior to being cut or otherwise made ready for use as an absorbent structure in an absorbent article. Dewatering can be brought about by compressing the foam to squeeze out residual water, by subjecting the foam, or the water therein, to elevated temperatures, or to microwave treatment, or by a combination of both compressing and water heating techniques. The dewatering step of HIPE foam processing will generally be carried out until the HIPE foam ready for use is as dry as practical.

The absorbent core of the absorbent article embodiments of this invention can consist solely of one or more of the foam structures herein. For example, the absorbent core may comprise a single unitary piece of foam shaped as desired or needed to best fit the type of absorbent article in which it is to be used. Alternatively, the absorbent core may comprise a plurality of foam pieces or particles which may be adhesively bonded together or which may simply be constrained into an unbonded aggregate held together by an overwrapping of envelope tissue or by means of the topsheet and backing sheet of the absorbent article.

The absorbent core of the absorbent articles herein can also comprise other, e.g., conventional, elements or materials in addition to one or more foam absorbent structures of the present invention. For example, absorbent articles herein may utilize an absorbent core which comprises a combination, e.g., an airlaid mixture, of particles or pieces of the foam absorbent structures herein and conventional absorbent materials such as a) wood pulp or other cellulosic fibers, and/or, b) particles or fibers of polymeric gelling agents.

In one embodiment involving a combination of the foam absorbent material herein and other absorbent materials, the absorbent articles herein may employ a multi-layer absorbent core configuration wherein a core layer containing one or more foam structures of this invention may be used in combination with one or more additional separate core layers comprising conventional absorbent structures or materials. Such conventional absorbent structures or materials, for example, can include air-laid or wet-laid webs of wood pulp or other cellulosic fibers. Such conventional structures may also comprise conventional, e.g., large cell, absorbent foams or even sponges.

As indicated hereinbefore, the fluid handling and mechanical characteristics of the specific foam absorbent structures herein render such structures especially suitable for use in absorbent articles in the form of disposable diapers. Disposable diapers comprising the foam absorbent structures of the present invention may be made by using conventional diaper making techniques, but by replacing or supplementing the pulp fibers or modified cellulosic core absorbents typically used in conventional diapers with one or more foam structures of the present invention. Foam structures of this invention may thus be used in diapers in single layer or, as noted hereinbefore, in various multiple layer core configurations.

Another preferred type of absorbent article which can utilize the foam absorbent structures of the present invention comprises form-fitting products such as training pants. Such form-fitting articles will generally include a nonwoven, flexible substrate fashioned into a chassis in the form of briefs or shorts. A foam absorbent structure according to the present invention can then be affixed in the crotch area of such a chassis in order to serve as an absorbent "core". This absorbent core will frequently be over-wrapped with envelope tissue or other liquid pervious, nonwoven material.

Such core overwrapping thus serves as the topsheet for the form-fitting absorbent article.

Tests Methods: Measuring Density and Compressional Rigidity of Foams

In describing the density and compressional rigidity of the foams comprised by the substantially non-wicking low density substance of the absorbent articles of the present invention, the following test methods are used:

First, a foam sample is prepared as follows. Foam samples of a predetermined size are cut from larger blocks of foam using a sharp reciprocating knife saw. Use of this or equivalent type of foam cutting device increases accuracy and specificity by serving to substantially eliminate edge flaws that may distort certain measurements made during the following test methods. Sample size specification will also generally include a dimension for sample caliper or thickness. Caliper or thickness measurements for purposes of the present invention should be made when the foam sample is under a confining pressure of 350 Pa.

Density of the foam is determined using ASTM Method No. D3574-86. In particular, density measurements made according to the procedure are carried out on foam samples which have been preconditioned in a certain manner as specified in that test.

Density is determined by measuring both the dry mass of a given foam sample and its volume at 22+2 degrees Celsius. Volume determination on larger foam samples are calculated from measurements of the sample dimensions made under no confining pressure. Dimensions of smaller foam samples may be measured using a dial-type gauge using a pressure on the dial foot of 350 Pa (0.05 psi).

Density is calculated as mass per unit volume. For purposes of this invention, density is generally expressed in terms of grams per cubic centimeter (g/cc).

Compressional rigidity is measured as follows. The amount of strain (% caliper reduction) produced in a foam sample, which has been saturated with synthetic urine, after stress in the form of a confining pressure has been applied to the sample is measured. The synthetic urine test fluid and equipment used to make measurements are all equilibrated in a constant temperature room heated to 37 degrees Celsius.

The foam samples are placed in a crystallizing dish and saturated to their free absorbent capacity with synthetic urine. A given saturated sample to be tested is then placed on a 25 mesh screen over a beaker, and a dial-type gauge suitable for making caliper measurements is positioned on the sample. Any gauge fitted with a foot having a surface area of at least 1 square inch (6.5 square centimeters) and capable of measuring caliper dimensions to 0.001 inches can be employed. Examples of such gauges are an Ames model 482 (Ames Co.; Waltham, Mass. ) or an Ono-Sokki model EG-225 (Ono-Sokki Co., Ltd.; Japan). Also utilized are weights which can be used with the dial gauge to produce a foot pressure on the foam sample of up to 6.9 kPa.

The saturated foam sample on the screen is subjected to a confining pressures for various lengths of time. At the end of the time, the dial gauge is used to measure the change in sample caliper which occurs as a consequence of the application of the confining pressure. From the initial and final caliper measurements, a percent strain induced can be calculated for the sample.

Due to the wide variety of materials which may be incorporated into the absorbent articles of the present invention, the present invention is not intended to be limited to any specific materials. The topsheet, backsheet, absorbent core and other components of the absorbent articles in accordance with various implementations of the present invention may comprise various materials. Persons of ordinary skill in the art would be readily able to select appropriate materials for use in the various components of the present invention based upon the materials.

In accordance with various implementations of the present invention, the absorbent core may contain one or more fibers, one or more polymers or combinations thereof. Non-limiting exemplary fibers which may be used in the articles of the present invention include, without limitation, cellulose fibers, cellulose acetate fibers, rayon fibers, Courtauld's LYOCEL fibers, polyacrylonitrile fibers, surface modified (hydrophilic) polyester fibers, surface modified polyolophin/polyester bicomponent fibers, surface modified polyester/polyester bicomponent fibers, cotton fibers or blends thereof. Preferably cellulose acetate, rayon, Courtauld's LYOCEL, polyacrylonitrile, cotton fibers and cotton linters or combinations thereof are used in the process of the present invention. More preferably, cellulose fibers are used as the fiber material in the present invention.

Other materials may be added to the fiber or pulp material which is optionally processed in a fiberizing apparatus, such as a hammermill. The additives may be added at any point in the process. Preferably, the additives are sprayed or injected into the airborne fibers prior to the depositing of the fibers on the forming surface 2. Non-limiting exemplary additives which may be incorporated into the process of the present invention include a polymer such as a super absorbent polymer (SAP), hydrophilic polymers, potato starch, corn starch, wheat starch or rice starch, or combinations thereof. Various different combinations of materials may be used as are known to persons of ordinary skill in the art and which are described in U.S. Pat. No. 6,068,620 which is herein incorporated by reference. Preferably, the mixtures incorporated in the invention are substantially homogenous mixtures or uniformly distributed mixtures. Absorbent articles in accordance with an implementation of the present invention are prepared using conventional methods and materials well known to persons of ordinary skill in the art, using the guidelines provided herein.

EXAMPLE 1

Comparative Study of Aborbent Articles

A comparative study was conducted on the absorbency of absorbent articles in accordance with an implementation of the present invention (Sample 1) and a representative conventional diaper (Pampers Baby Dry). The results of the study are displayed in Table 1 below:

TABLE 1

| TESTED DIAPER | PRESSURE (PSI): DOSE: | 0.1 1 | 0.1 2 | 0.1 3 | 0.5 1 | 0.5 2 | 0.5 3 |
|---|---|---|---|---|---|---|---|
| Sample 1 | Absorption Times (s) | 2 | 2 | 2 | 2 | 3 | 5 |
| Pampers Baby Dry | Absorption Times (s) | 4 | 4 | 9 | 5 | 10 | >600 |

The present invention has been described in connection with the preferred embodiments. These embodiments, however, are merely for example and the invention is not restricted thereto. Any examples described herein are illustrative of preferred embodiments of the inventive subject matter and are not to be construed as limiting the inventive subject matter thereto. It will be understood by those skilled in the art that other variations and modifications can easily be made within the scope of the invention as defined by the appended claims.

What is claimed is:

1. An absorbent article comprising:
a substantially impermeable backsheet;
a permeable topsheet;
a substantially non-wicking low density substance disposed between the substantially impermeable backsheet and the permeable topsheet, said substantially non-wicking low density substance comprising a foam having a density of no greater than about 0.01 g/cc and a compressional rigidity at about 10% strain of at least about 4 kPa; and
wherein the foam has a vertical wicking rate of no greater than 2 seconds as measured by the time for each of three successive doses of colored synthetic urine from a reservoir to wick a vertical distance of 5 cm through a test strip of the foam under a pressure of 0.1 psi at 37° C.

2. The absorbent article of claim 1, wherein the foam comprises a polymer.

3. The absorbent article of claim 2, wherein the polymer is selected from the group consisting of a polyurethane, a polyethylene, a polypropylene, a polyacrylic, a polyamide, a polyvinyl chloride, an epoxy, a polystyrene, a melamine-formaldehyde polymer and combinations thereof.

4. The absorbent article of claim 2, wherein the polymer is a polyurethane.

5. The absorbent article of claim 2, wherein the polymer is a melamine-formaldehyde polymer.

6. The absorbent article of claim 1, wherein the foam has a density no greater than about 0.007 g/cc.

7. The absorbent article of claim 1, wherein the foam has a density no greater than about 0.005 g/cc.

8. The absorbent article of claim 1, wherein the foam has a density no greater than about 0.004 g/cc.

9. The absorbent article of claim 1, wherein the foam has a compressional rigidity at 10% strain of at least about 4.5 kPa.

10. The absorbent article of claim 1, wherein the foam has a compressional rigidity at 10% strain of at least about 5.0 kPa.

11. The absorbent article of claim 1, wherein the foam has a compressional rigidity at 10% strain of at least about 5.5 kPa.

12. The absorbent article of claim 1, wherein the foam has a vertical wicking bsorbent capacity of about 0.

13. The absorbent article of claim 1, wherein the foam additionally comprises stabilizing agent.

14. The absorbent article of claim 13, wherein the stabilizing agent is selected from the group consisting of formaldehyde, glutaraldehyde, glyoxal, glyoxylic acid, oxydisuccinic acid, citric acid and combinations thereof.

15. The absorbent article of claim 13, wherein the stabilizing agent is a crosslinking agent or combinations thereof.

16. The absorbent article of claim 15, wherein the crosslinking agent is selected from the group consisting of a dialdehyde having 2 to 8 carbon atoms, a monoaldehyde having an acid functionality and 2 to 8 carbon atoms, a polycarboxylic acid having 2 to 9 carbon atoms, and combinations thereof.

17. The absorbent article of claim 1, wherein the foam comprises melamine resin and formaldehyde.

18. The absorbent article of claim 1, wherein the substantially non-wicking low density substance additionally comprises a surfactants, a filler, an additive or a combination thereof.

19. The absorbent article of claim 18, wherein the additive is selected from the group consisting of a flame retardant, a reinforcing agent, an auxiliary blowing agent, a medicament, a fragrance, a colorant, a cleaner, an abrasive and a combination thereof.

20. The absorbent article of claim 1, wherein the absorbent article is a diaper, incontinent brief, training pant, diaper holder, diaper liner, sanitary napkin, hygienic garment or combination thereof.

21. The absorbent article of claim 1, wherein the substantially non-wicking low density substance is thermo-formed.

22. The absorbent article of claim 1, wherein the substantially non-wicking low density substance is thermo-bonded to the substantially impermeable backsheet or the permeable topsheet.

23. An absorbent article comprising:
a substantially impermeable backsheet;
a permeable topsheet;
an absorbent core disposed between the substantially impermeable backsheet and the permeable topsheet; and
a substantially non-wicking low density substance disposed on a surface of the absorbent core, said substantially non-wicking low density substance comprising a foam having a density of no greater than about 0.01 g/cc and a compressional rigidity at about 10% strain of at least about 4 kPa; and
wherein the foam has a vertical wicking rate of no greater than 2 seconds as measured by the time for each of three successive doses of colored synthetic urine from a reservoir to wick a vertical distance of 5 cm through a test strip of the foam under a pressure of 0.1 psi at 37° C.

24. The absorbent article of claim 23, wherein the absorbent core is a thin Dry Formed Composite (DFC)-type core.

25. The absorbent article of claim 23, wherein the substantially non-wicking low density substance is thermo-formed.

26. The absorbent article of claim 23, wherein the substantially non-wicking low density substance is thermo-bonded to the substantially impermeable backsheet or the permeable topsheet.

27. An absorbent garment comprising:
a substantially impermeable backsheet and a permeable topsheet defining a front waste portion and a rear waste portion, said front waste portion and said rear waste portion cooperating to form a waste opening;
a crotch region formed between the front waste portion and the rear waste portion;
a pair of leg openings on opposed sides of the crotch region;
an absorbent core; disposed between the substantially impermeable backsheet and the permeable topsheet at the crotch region; and
a substantially non-wicking low density substance disposed on the absorbent core, said substantially non-wicking low density substance comprising a foam having a density of no greater than about 0.01 g/cc and a compressional rigidity at about 10% strain of at least about 4 kPa; and
wherein the foam has a vertical wicking rate of no greater than 2 seconds as measured by the time for each of three successive doses of colored synthetic urine from a reservoir to wick a vertical distance of 5 cm through a test strip of the foam under a pressure of 0.1 psi at 37° C.

28. The absorbent article of claim 27, wherein the foam comprises a polymer.

29. The absorbent article of claim 28, wherein the polymer is selected from the group consisting of a polyurethane, a polyethylene, a polypropylene, a polyacrylic, a polyamide, a polyvinyl chloride, an epoxy, a polystyrene, a melamine-formaldehyde polymer and combinations thereof.

30. The absorbent article of claim 28, wherein the polymer is a polyurethane.

31. The absorbent article of claim 28, wherein the polymer is a melamine-formaldehyde polymer.

32. The absorbent article of claim 27, wherein the foam has a density no greater than about 0.007 g/cc.

33. The absorbent article of claim 27, wherein the foam has a density no greater than about 0.005 g/cc.

34. The absorbent article of claim 27, wherein the foam has a density no greater than about 0.004 g/cc.

35. The absorbent article of claim 27, wherein the foam has a compressional rigidity at 10% strain of at least about 4.5 kPa.

36. The absorbent article of claim 27, wherein the foam has a compressional rigidity at 10% strain of at least about 5.0 kPa.

37. The absorbent article of claim 27, wherein the foam has a compressional rigidity at 10% strain of at least about 5.5 kPa.

38. The absorbent article of claim 27, wherein the foam has a vertical wicking absorbent capacity of about 0.

39. The absorbent article of claim 27, wherein the foam additionally comprises a stabilizing agent.

40. The absorbent article of claim 39, wherein the stabilizing agent is selected from the group consisting of formaldehyde, glutaraldehyde, glyoxal, glyoxylic acid, oxydisuccinic acid, citric acid and combinations thereof.

41. The absorbent article of claim 39, wherein the stabilizing agent is a crosslinking agent or combinations thereof.

42. The absorbent article of claim 41, wherein the crosslinking agent is selected from the group consisting of a dialdehyde having 2 to 8 carbon atoms, a monoaldehyde having an acid functionality and 2 to 8 carbon atoms, a polycarboxylic acid having 2 to 9 carbon atoms, and combinations thereof.

43. The absorbent article of claim 27, wherein the foam comprises melamine resin and formaldehyde.

44. The absorbent article of claim 27, wherein the substantially non-wicking low density substance additionally comprises a surfactants, a filler, an additive or a combination thereof.

45. The absorbent article of claim 44, wherein the additive is selected from the group consisting of a flame retardant, a reinforcing agent, an auxiliary blowing agent, a medicament, a fragrance, a colorant, a cleaner, an abrasive and a combination thereof.

46. The absorbent article of claim 27, wherein the absorbent article is a diaper.

47. The absorbent article of claim 27, wherein the substantially non-wicking low density substance is thermoformed.

48. The absorbent article of claim 27, wherein the substantially non-wicking low density substance is thermobonded to the substantially impermeable backsheet or the permeable topsheet.

49. A composition for absorbent articles comprising:
a foam comprising a polymer selected from the group consisting of a polyurethane, a polyethylene, a polypropylene, a polyacrylic, a polyamide, a polyvinyl chloride, an epoxy, a polystyrene, a melamine-formaldehyde polymer and combinations thereof, said foam having a density of no greater than about 0.01 g/cc and a compressional rigidity at about 10% strain of at least about 4 kPa; and
wherein the foam has a vertical wicking rate of no greater than 2 seconds as measured by the time for each of three successive doses of colored synthetic urine from a reservoir to wick a vertical distance of 5 cm through a test strip of the foam under a pressure of 0.1 psi at 37° C.

50. A composition for absorbent articles prepared by a process comprising:
combining a foaming agent and a stabilizing agent to form a High Internal Phase Emulsion (HIPE);
polymerizing the High Internal Phase Emulsion (HIPE) to form a substantially non-wicking low density polymer foam, said substantially non-wicking low density polymer foam having a density of no greater than about 0.01 g/cc and a compressional rigidity at about 10% strain of at least about 4 kPa; and
wherein the substantially non-wicking low density polymer foam has a vertical wicking rate of no greater than 2 seconds as measured by the time for each of three successive doses of colored synthetic urine from a reservoir to wick a vertical distance of 5 cm through a test strip of the substantially non-wicking low density polymer foam under a pressure of 0.1 psi at 37° C.

51. The composition of claim 50, wherein the forming agent is selected from the group consisting of melamine resin and formaldehyde.

52. The composition of claim 50, wherein the stabilizing agent is selected from the group consisting of formaldehyde, glutaraldehyde, glyoxal, glyoxylic acid, oxydisuccinic acid, citric acid and combinations thereof.

53. The composition of claim 50, wherein the composition is in roll form.

54. A method of preparing an absorbent article comprising:
combining a foaming agent and a stabilizing agent to form a High Internal Phase Emulsion (HIPE);
polymerizing the High Internal Phase Emulsion (HIPE) to form a substantially non-wicking polymer foam, said substantially non-wicking polymer foam having a density of no greater than about 0.01 g/cc and a compressional rigidity at about 10% strain of at least about 4 kPa; and
wherein the substantially non-wicking polymer foam has a vertical wicking rate of no greater than 2 seconds as measured by the time for each of three successive doses of colored synthetic urine from a reservoir to wick a vertical distance of 5 cm through a test strip of the substantially non-wicking polymer foam under a pressure of 0.1 psi at 37° C.

55. A method of improving absorbency of an absorbent article comprising:
applying a substantially non-wicking layer to a surface of an absorbent core, said substantially non-wicking layer comprising a foam having a density of no greater than about 0.01 g/cc and a compressional rigidity at about 10% strain of at least about 4 kPa, said foam having a vertical wicking rate of no greater than 2 seconds as measured by the time for each of three successive doses of colored synthetic urine from a reservoir to wick a vertical distance of 5 cm through a test strip of the substantially non-wicking low density substance under a pressure of 0.1 psi at 37° C.; and
disposing the absorbent core between a substantially impermeable backsheet and a permeable topsheet.

* * * * *